United States Patent [19]

Cauwet et al.

[11] Patent Number: 5,637,306
[45] Date of Patent: Jun. 10, 1997

[54] USE IN COSMETICS OR IN TOPICAL APPLICATION OF AN AQUEOUS DISPERSION BASED ON NONVOLATILE ORGANOPOLYSILOXANES AND ON A CROSSLINKED METHACRYLOYLOXYETHYL-TRIMETHYLAMMONIUM CHLORIDE POLYMER OF HOMOPOLYMER OR COPOLYMER WITH ACRYLAMIDE TYPE

[75] Inventors: Danièle Cauwet, Paris; Claude Dubief, Le Chesnay, both of France

[73] Assignee: L'Oreal, Paris, France

[21] Appl. No.: 513,984

[22] PCT Filed: Mar. 15, 1994

[86] PCT No.: PCT/FR94/00275

§ 371 Date: Sep. 13, 1995

§ 102(e) Date: Sep. 13, 1995

[87] PCT Pub. No.: WO94/21224

PCT Pub. Date: Sep. 29, 1994

[30] Foreign Application Priority Data

Mar. 16, 1993 [FR] France ................. 93 02987

[51] Int. Cl.⁶ ................. A61K 7/06; A61K 7/48
[52] U.S. Cl. ................. 424/401; 424/70.12; 424/70.17; 424/78.03; 424/DIG. 2
[58] Field of Search .................. 424/401, 70.1, 424/70.11, 70.12, 70.17, 78.03, DIG. 2

[56] References Cited

U.S. PATENT DOCUMENTS

| 5,160,730 | 11/1992 | Dubief et al. | 424/59 |
| 5,221,530 | 6/1993 | Janchitraponvej et al. | 424/70.11 |

FOREIGN PATENT DOCUMENTS

| 0219830 | 4/1987 | European Pat. Off. . |
| 0424260 | 4/1991 | European Pat. Off. . |
| 0524434 | 1/1993 | European Pat. Off. . |
| WO86/02546 | 5/1986 | WIPO . |
| WO92/10162 | 6/1992 | WIPO . |

*Primary Examiner*—John C. Bleutge
*Assistant Examiner*—Robert H. Harrison
*Attorney, Agent, or Firm*—Jacobson, Price, Holman & Stern, PLLC

[57] ABSTRACT

The cosmetic or topical use of an aqueous dispersion at least of a cosmetically acceptable aqueous medium containing an acrylamide homopolymeric or copolymer cross-linked methacryloyloxyethyl trimethylammonium chloride polymer, and a non-volatile organopolysiloxane selected from polyalkylsiloxanes, polyarylsiloxanes, polyalkylarylsiloxanes, silicone resins and gums, and organomodified polysiloxanes, with the exception of polysiloxanes comprising polyethyleneoxy and/or polypropyleneoxy, carboxylate or bisulfite groupings, is disclosed.

19 Claims, No Drawings

USE IN COSMETICS OR IN TOPICAL APPLICATION OF AN AQUEOUS DISPERSION BASED ON NONVOLATILE ORGANOPOLYSILOXANES AND ON A CROSSLINKED METHACRYLOYLOXYETHYL-TRIMETHYLAMMONIUM CHLORIDE POLYMER OF HOMOPOLYMER OR COPOLYMER WITH ACRYLAMIDE TYPE

The invention relates to the use in cosmetics or in topical application of an aqueous dispersion based on nonvolatile organopolysiloxanes and on a crosslinked methacryloyloxyethyltrimethylammonium chloride polymer of homopolymer or copolymer with acrylamide type.

Silicone oils are already used in cosmetics as a lubricant in hair and skin treatment compositions. They are mainly polydimethylsiloxanes.

Cationic surfactants or polymers have been used for a long time in order to contribute softness to hair or to the skin or alternatively to facilitate disentangling of hair. Cationic compounds have the disadvantage, after repeated applications, of making the hair lank, giving it a sticky appearance, or of producing a sticky effect on the skin.

The Applicant Company has discovered, surprisingly, that the use of an aqueous dispersion based on nonvolatile organopolysiloxanes and on a crosslinked methacryloyloxyethyltrimethylammonium chloride polymer of homopolymer or copolymer with acrylamide type for the treatment of hair makes it possible to obtain shiny, silky and light hair whose disentangling, softness and hold properties are substantially improved. In addition, the drying time of the hair is shorter.

The use of this aqueous dispersion in the treatment of the skin also makes it possible to confer a soft feel on the latter, without a sticky effect.

The aqueous dispersions used in cosmetics or in topical application according to the present invention are spread over the skin and over hair much more easily than the compositions of the prior art based on cationic compounds.

The Applicant Company has also discovered that the cosmetic compositions in aqueous dispersion form according to the present invention were remarkably stable and that their cosmetic properties were retained even after several successive applications.

One subject of the invention therefore comprises the use, in the cosmetic treatment of hair or of the skin or in topical application, of an aqueous dispersion containing at least one organopolysiloxane defined hereinbelow and of [sic] one crosslinked methacryloyloxyethyltrimethylammonium chloride polymer of homopolymer or copolymer with acrylamide type.

Another subject of the invention relates to cosmetic or dermatological compositions for the treatment of hair or of the skin in the form of aqueous dispersions.

Another subject of the invention relates to processes for the cosmetic treatment of hair or of the skin using these compositions, according to the application desired.

Other subjects of the invention will become apparent in the light of the description and examples which follow.

The main subject of the present invention is the use, in the cosmetic treatment of hair or of the skin or in topical application, of an aqueous dispersion, characterized in that the latter contains at least, in a cosmetically or physiologically acceptable aqueous medium, one crosslinked methacryloyloxyethyltrimethylammonium chloride polymer of homopolymer or copolymer with acrylamide type and one nonvolatile organopolysiloxane chosen from polyalkylsiloxanes, polyarylsiloxanes, polyalkylarylsiloxanes, silicone gums and resins or organomodified polysiloxanes, with the exception of polysiloxanes carrying polyethyleneoxy and/or polypropyleneoxy, or carboxylate or bisulfite, groups.

The organopolysiloxanes used in the dispersions according to the present invention are nonvolatile organopolysiloxane oils or organosiloxane gum or resin organic solutions or alternatively emulsions or microemulsions containing these organopolysiloxanes.

Mention may be made, among the polyalkylsiloxanes, mainly of linear polydimethylsiloxanes: either, containing end trimethylsilyl groups, such as, for example, and without implied limitation, Silbione oils of the 70047 series marketed by Rhône-Poulenc, 47 V 500,000 oil from Rhône-Poulenc or certain Viscasil [sic] from General Electric, or containing end trihydroxysilyl groups, such as the oils of the 48 V series from Rhône-Poulenc.

Mention may also be made, in this class of polyalkylsiloxanes, of polyalkylsiloxanes sold by the Company Goldschmidt under the names Abilwax 9800 and Abilwax 9801, which are polyalkyl($C_1$–$C_{20}$)siloxanes.

Mention may be made, among the polyalkylarylsiloxanes, of linear and/or branched polydimethylphenylsiloxanes or polydimethyldiphenylsiloxanes, with a viscosity of $10^{-5}$ to $5.10^{-2}$ m$^2$/s at 25° C., such as, for example:

Rhodorsil 763 oil from Rhône-Poulenc,

Silbione oils of the 70641 series from Rhône-Poulenc, such as Silbione 70641 V 30 and 70641 V 200 oils from Rhône-Poulenc, the product DC 556 Cosmetic Grad Fluid from Dow Corning, silicones of the PK series from Bayer, such as PK20, silicones of the PN and PH series from Bayer, such as PN 1000 and PH 1000, certain oils of the SF series from General Electric, such as SF 1250, SF 1265, SF 1154 and SF 1023, 618 V 25000 oil from Rhône-Poulenc.

The silicone gums in accordance with the present invention are polydiorganosiloxanes with a high molecular mass of between 200,000 and 1,000,000, used alone or as a mixture in a solvent chosen from polydimethylsiloxane (PDMS) oils, polyphenylmethylsiloxane (PPMS) oils, isoparaffins, methylene chloride, pentane, dodecane, tridecane, tetradecane or their mixtures.

Mention is made, for example, of the following compounds:

polydimethylsiloxane, optionally hydroxylated at the chain end, poly [(dimethylsiloxane)/(methylvinylsiloxane)], poly [(dimethylsiloxane)/(diphenylsiloxane)], poly [(dimethylsiloxane)/(phenylmethylsiloxane)], poly [(dimethylsiloxane)/(diphenylsiloxane)/(methylvinylsiloxane)].

Mention may be made, for example, without implied limitation, of the following mixtures:

1) the mixtures formed from a polydimethylsiloxane hydroxylated at the chain end (Dimethiconol according to the CTFA nomenclature) and from a cyclic polydimethylsiloxane (Cyclomethicone according to the CTFA nomenclature), such as the product Q2 1401 sold by the Company Dow Corning;

2) the mixtures formed from a polydimethylsiloxane gum with a cyclic silicone, such as the product SF 1214 Silicone Fluid from General Electric, which is an SE 30 gum with a MW of 500,000 dissolved in SF 1202 Silicone Fluid (decamethylcyclopentasiloxane);

3) the mixtures of two PDMS of different viscosities, in particular of a PDMS gum and of a PDMS oil, such as the products SF 1236 and CF 1241 from the Company General Electric. The product SF 1236 is the mixture of an SE 30 gum defined hereinabove, with a viscosity of 20 $m^2/s$, and of an SF 96 oil, with a viscosity of $5.10^{-6} m^2/s$ (15% of SE 30 gum and 85% of SF 96 oil).

The product CF 1241 is the mixture of an SE 30 gum (33%) and of a PDMS (67%) with a viscosity of $10^{-3} m^2/s$.

The organopolysiloxane resins which can be used in accordance with the invention are crosslinked siloxane systems containing the units: $R_2SiO_{2/2}$, $RSiO_{3/2}$ and $SiO_{4/2}$, in which R represents a hydrocarbon group having 1 to 6 carbon atoms or a phenyl group. The particularly preferred products among these are those in which R denotes a lower alkyl radical or a phenyl radical.

Mention may be made, among these resins, of the product sold under the name Dow Corning 593 or of those sold under the names Silicone Fluid SS 4230 and SS 4267 by the Company General Electric and which are "dimethyl/trimethylpolysiloxane".

The organomodified silicones in accordance with the present invention are silicones as defined above containing, in their general structure, one or a number of organofunctional groups directly attached to the siloxane chain or attached via a hydrocarbon radical.

Mention is made, for example, of the silicones containing:

a) fluorinated groups such as trifluoroalkyls, such as, for example, those sold by the Company General Electric under the names "FF 150 Fluorosilicone Fluid" or by the Company Shin Etsu under the names X-22-819, X-22-820, X-22-821 and X-22-822;

b) hydroxyacylamino groups, such as those described in European Patent Application EPA-0,342,834 and in particular the silicone sold by the Company Dow Corning under the name Q2-8413;

c) thiol groups, as in the silicones X 2-8360 from Dow Corning or GP 72A and GP 71 from Genesee;

d) substituted or unsubstituted amino groups, as in GP4 Silicone Fluid from Geneses, GP 7100 from Genesee, Q2 8220 from Dow Corning, AFL 40 from Union Carbide or the silicone known as "Amodimethicone" in the CTFA dictionary;

e) hydroxylated groups, such as the polyorganosiloxanes containing hydroxyalkyl and in particular γ-hydroxypropyl functional groups, described in French Patent Application No. FR-85 16334;

f) alkoxylated groups, as in Silicone copolymer F 755 from SWS Silicones and the products Abilwax 2428, Abilwax 2434 and Abilwax 2440 from the Company Goldschmidt;

g) acyloxyalkyl groups, such as, for example, the polyorganopolysiloxanes described in French Patent Application No. 88 17433, and in particular γ-stearoyloxypropyl groups;

h) quaternaryammonium groups, as in the products X2 81 08 and X2 81 09 or the product Abil K 3270 from the Company Goldschmidt;

i) amphoteric or betaine groups, such as in the product sold by the Company Goldschmidt under the name Abil B 9950;

The polyorganosiloxanes used according to the invention are present in the aqueous dispersion in a proportion of between 0.2 and 50% by weight, preferably between 1 and 30% by weight, with respect to the total weight of the dispersion.

The crosslinked methacryloyloxyethyltrimethylammonium chloride polymers used according to the invention are more particularly chosen from the polymers obtained by homopolymerization of dimethylaminoethyl methacrylate quaternized by methyl chloride or by copolymerization of acrylamide with dimethylaminoethyl methacrylate quaternized by methyl chloride, the homo- or copolymerization being followed by crosslinking by a compound possessing olefinic unsaturation, in particular methylenebisacrylamide.

Use is more particularly made of a crosslinked acrylamide-methacryloyloxyethyltrimethylammonium chloride (20/80 by weight) copolymer in the form of a dispersion containing 50% by weight of the said copolymer in mineral oil. This dispersion is marketed under the name of Salcare SC92 by the Company Allied Colloids. Use is also made of a crosslinked methacryloyloxyethyltrimethylammonium chloride homopolymer containing approximately 50% by weight of the homopolymer in mineral oil. This dispersion is marketed under the name Salcare SC95 by the Company Allied Colloids.

The crosslinked polymers as defined above are present in the aqueous dispersions of the invention at active material concentrations of between 0.05 and 10% by weight, and preferably between 0.1 and 6% by weight, with respect to the total weight of the dispersion.

Among the polyorganosiloxanes, preference is given according to the invention to the use of silicones organomodified by thiol groups, substituted or unsubstituted amino groups or fluorinated groups and of silicone gums and resins.

Among the crosslinked polymers, preference is given, according to the invention, to the use of a crosslinked copolymer of acrylamide and of methacryloyloxyethyltrimethylammonium chloride (20/80).

The dispersions in accordance with the invention can additionally contain adjuvants commonly used in cosmetics or in dermatology, such as fragrances, dyes, preservatives, stabilizers, sequestering agents, waxes, pearlescent agents, vegetable, animal or synthetic oils, perfluoropolyethers, ceramides, sunscreens, agents for combating free radicals, anionic, nonionic, amphoteric or cationic surfactants, polymers, proteins, foam stabilizers or propellants, according to the application envisaged.

The cosmetic compositions intended for the treatment of hair in accordance with the invention can be used in particular as a shampoo, as a product to be rinsed out, to be applied before or after a shampoo, before, during or after dyeing or bleaching, before or after a permanent wave or hair straightening or in a lotion to be applied during the perming operation or as a nonrinsed styling product, as in hair-setting or blow-drying lotions.

The cosmetic compositions in accordance with the present invention intended for the treatment and care of the skin can be in the form of a product for the bath or the shower, of a tanning product, of a product for shaving, of a scented lotion, of a cream or milk for caring for the skin or of antisun compositions.

When the compositions according to the invention contain surfactants, the latter are present in a concentration of between 5 and 30%, in the case of shampoos or shower gels, and in a proportion of less than 5% by weight with respect to the total weight of the composition, in the case of rinsed compositions to be applied after shampoos or of nonrinsed compositions.

The compositions in accordance with the present invention can be applied in dermatology. They contain, in an effective amount, a substance which is active at the dermatological level, such as, for example, vitamin A, carotenoids, proteins, natural pigments, retinoids, depigmenting agents, antiseborrheic or antiacne substances, antiinflammatories or antidandruff agents.

The cosmetic or dermatological compositions according to the present invention have a pH of between 3 and 10 and preferably between 3 and 7. This pH can be adjusted by basifying or acidifying agents commonly used in cosmetics and in dermatology.

A process for the cosmetic treatment of hair according to the invention consists in applying the compositions as defined above to hair, according to the use envisaged (shampoo, treatment to be rinsed out, rinsing-free styling treatment), without it being necessary to observe an exposure time, and optionally in rinsing.

A process for the cosmetic treatment of the skin according to the invention consists in applying a composition as defined above to the latter, depending on the use envisaged (bath, shower, tanning products, products for shaving, scented lotions or care creams or milks), and optionally in rinsing.

The examples which follow are intended to illustrate the present invention without having any limiting nature.

EXAMPLE 1

A conditioner with the following composition is prepared:

| | |
|---|---|
| Dispersion in mineral oil of crosslinked acrylamide-methacryloyloxyethyltrimethylammonium chloride copolymer, sold as 50% copolymer under the name "Salcare SC 92" by the Company Allied Colloids | 0.5 g as copolymer |
| Polydimethyldiphenylsiloxane (90/10) α,ω-disilanol, sold under the name "618 V 25000 Oil" by the Company Rhône-Poulenc | 10 g |
| Preservative q.s. | |
| Spontaneous pH = 5 | |
| Demineralized water q.s. for | 100 g |

EXAMPLE 2

A conditioner with the following composition is prepared:

| | |
|---|---|
| Dispersion in mineral oil of crosslinked acrylamide-methacryloyloxyethyltrimethylammonium chloride copolymer, sold as 50% copolymer under the name "Salcare SC 92" by the Company Allied Colloids | 0.5 g as copolymer |
| Polymethyltrifluoropropylsiloxane, sold under the name "FF 150-10M" by the Company General Electric | 1 g |
| Preservative q.s. | |
| Spontaneous pH = 4.5 | |
| Demineralized water q.s. for | 100 g |

EXAMPLE 3

A conditioner with the following composition is prepared:

| | |
|---|---|
| Dispersion in mineral oil of crosslinked acrylamide-methacryloyloxyethyltrimethylammonium chloride copolymer, sold as 50% copolymer under the name "Salcare SC 92" by the Company Allied Colloids | 0.5 g as copolymer |
| Polydimethyl/methyltrifluoropropylsiloxane, sold under the name "X-22-820" by the Company Shin Etsu | 1 g |
| Preservative q.s. | |
| Spontaneous pH = 4 | |
| Demineralized water q.s. for | 100 g |

EXAMPLE 4

A conditioner with the following composition is prepared:

| | |
|---|---|
| Salcare SC 92 | 0.75 g as copolymer |
| PDMS, sold under the name "47 V 500,000 Oil" by the Company Rhône-Poulenc | 0.75 g |
| Methylglucose oxyethylenated with 20 mol of ethylene oxide | 1.05 g |
| Preservatives q.s. | |
| Spontaneous pH = 3.8 | |
| Demineralized water q.s. for | 100 g |

EXAMPLE 5

A conditioner with the following composition is prepared:

| | |
|---|---|
| Salcare SC 92 | 1.96 g as copolymer |
| PDMS, sold under the name "47 V 500,000 Oil" by the Company Rhône-Poulenc | 0.25 g |
| Mineral oil | 5 g |
| Preservatives | 0.1 g |
| Spontaneous pH = 3.6 | |
| Demineralized water q.s. for | 100 g |

EXAMPLE 6

A shampoo with the following composition is prepared:

| | |
|---|---|
| Salcare SC 92 | 0.2 g AM |
| PDMS, sold under the name "47 V 500,000 Oil" by the Company Rhône-Poulenc | 2 g |
| Sodium lauryl ether sulfate containing 2.2 mol of ethylene oxide as an aqueous solution containing 28% of AM | 16.8 g AM |
| Cocoylbetaine as an aqueous solution containing 32% of AM | 2.6 g AM |
| Cetyl 2-hydroxycetylstearyl ether/cetyl alcohol | 2.5 g |
| Coconut acid monoisopropanolamide | 1.5 g |
| Preservative, fragrance q.s. | |
| NaOH q.s. pH = 6.5 | |
| Water q.s. for | 100 g |

EXAMPLE 7

A suntan product with the following composition was prepared:

| | |
|---|---|
| Salcare SC 95 | 1.5 g AM |
| PDMS (Silbione 70047 V 300 Rhône- | 5 g |

-continued

| | |
|---|---|
| Poulenc) | |
| Hydrogenated polydecene (Ethylflo 364 NF from Ethyl Corp.) | 5 g |
| 2-Ethylhexyl para-methoxycinnamate (Parsol MCX from Givaudan) | 4 g |
| Triethanolamine q.s. pH = 7 | |
| Preservative q.s. | |
| Water q.s. for | 100 g |

We claim:

1. A method for cosmetic treatment, comprising the topical application of an aqueous dispersion, said dispersion containing, in a cosmetically or physiologically acceptable aqueous medium, at least one nonvolatile organopolysiloxane selected from the group consisting of polyalkylsiloxanes, polyarylsiloxanes, polyalkylarylsiloxanes, modified and unmodified polysiloxanes, silicone gums and resins, and organomodified polysiloxanes, with the exception of polysiloxanes carrying polyethyleneoxy and/or polypropyleneoxy or carboxylate or bisulfite groups, and one crosslinked methacryloyloxyethyltrimethylammonium chloride homopolymer or acrylamide-methacryloyloxyethyltrimethylammonium chloride copolymer.

2. Method according to claim 1, characterized in that the organopolysiloxane contains, in its general structure, one or a number of organofunctional group(s) directly attached to the siloxane chain or attached via a hydrocarbon radical and is selected from the polyorganosiloxanes containing:
   a) fluorinated groups;
   b) hydroxyacylamino groups;
   c) thiol groups;
   d) substituted or unsubstituted amino groups;
   e) hydroxyalkyl groups;
   f) alkoxylated groups;
   g) acyloxyalkyl groups;
   h) quaternary ammonium groups or
   i) amphoteric or betaine groups.

3. Method according to claim 1, characterized in that the acrylamide-methacryloyloxyethyltrimethylammonium chloride copolymer is obtained by copolymerization of acrylamide and of dimethylaminoethyl methacrylate quaternized by methyl chloride and in that the homopolymer is obtained by homopolymerization of dimethylaminoethyl methacrylate quaternized by methyl chloride, the polymerization being followed by crosslinking by a compound possessing olefinic unsaturation.

4. Method according to claim 1, characterized in that the crosslinked acrylamide-methacryloyloxyethyltrimethylammonium chloride (20/80 by weight) copolymer is in the form of a dispersion containing 50% by weight of the said copolymer in mineral oil.

5. Method according to claim 1, characterized in that the crosslinked methacryloyloxyethyltrimethylammonium chloride homopolymer is in the form of a dispersion in mineral oil.

6. Method according to claim 1, characterized in that the organopolysiloxane is present in proportions of between 0.2 and 50% by weight with respect to the total weight of the dispersion and the crosslinked polymer is present in proportions of between 0.05 and 10% by weight.

7. Method according to claim 3, wherein the compound possessing olefinic unsaturation is methylenebisacrylamide.

8. Method according to claim 1, characterized in that the organopolysiloxane is selected from the group consisting of:

A) polyalkyl ($C_1$–$C_{20}$) siloxanes; linear polydimethylsiloxanes containing end trimethylsilyl groups and linear polydimethylsiloxanes containing end trihydroxysilyl groups;

B) linear and/or branched polydimethylphenylsiloxanes or polydimethyldiphenylsiloxanes, with a viscosity of $10^{-5}$ to $5.10^{-2}$ M$^2$/s at 25° C.;

C) gums used alone or in the form of a mixture in a solvent, selected from the group consisting of the following compounds:
   polydimethylsiloxane, optionally hydroxylated at the chain end,
   poly [(dimethylsiloxane)/(methylvinylsiloxane)],
   poly [(dimethylsiloxane)/(diphenylsiloxane)],
   poly [(dimethylsiloxane)/(phenylmethylsiloxane)],
   poly [(dimethylsiloxane)/(diphenylsiloxane)/(methylvinylsiloxane)];

and the following mixtures;
   the mixtures formed from a polydimethylsiloxane hydroxylated at the chain end and from a cyclic polydimethylsiloxane;
   the mixtures formed from a polydimethylsiloxane gum and from a cyclic silicone;
   the mixtures of two polydimethylsiloxanes of different viscosities; and D) the organopolysiloxane resins containing the $R_2SiO_{2/2}$, $RSiO_{3/2}$ and $SiO_{4/2}$ units, in which R represents a hydrocarbon group having 1 to 6 carbon atoms or a phenyl group.

9. Cosmetic composition in the form of an aqueous dispersion for the treatment of hair or of the skin, containing at least one non-volatile organopolysiloxane selected from the group consisting of polyalkylsiloxanes, polyarylsiloxanes, polyalkylarylsiloxanes, modified or unmodified polysiloxanes, silicone gums and resins, and organomodified polysiloxanes, with the exception of polysiloxanes carrying polyethyleneoxy and/or polypropyleneoxy or carboxylate or bisulfite groups, and one crosslinked methacryloyloxyethyltrimethyl ammonium chloride homopolymer or acrylamide-methacryloyloxyethyltrimethyl ammonium chloride copolymer.

10. Composition according to claim 9, characterized in that it additionally contains adjuvants commonly used in cosmetics selected from fragrances, dyes, preservatives, stabilizers, waxes or vegetable, animal or synthetic oils, pearlescent agents, proteins, conditioning agents, anionic, nonionic, amphoteric or cationic surfactants, sequestering agents, foam stabilizers, polymers, sunscreens, propellants, perfluoropolyethers, ceramides and agents for combating free radicals.

11. Composition according to claim 9, characterized in that it has a pH of between 3 and 10.

12. Composition according to claim 9 for the treatment of hair, characterized in that it is provided in the form of a shampoo, of a product to be rinsed out, to be applied before or after a shampoo, before, during or after dyeing or bleaching, before or after a permanent wave or hair straightening, in a lotion to be applied during the perming operation, or as nonrinsed styling products.

13. Composition according to claim 9 for the treatment of the skin, characterized in that it is provided as a bath or shower product, of a tanning product, of an antisun composition, of a shaving product, of a care cream or milk or of a scented lotion.

14. Composition according to claim 9, characterized in that it is provided in the form of a shampoo or of a bath or shower product containing from 5 to 30% by weight of surfactants with respect to the total weight of the composition.

15. Composition according to claim 9, characterized in that it is provided in the form of a product to be rinsed out to be applied after a shampoo or of a nonrinsed styling product and in that it contains surfactants in a proportion of less than 5% by weight with respect to the total weight of the composition.

16. Composition according to claim 9 having a pH from 3 to 7.

17. Method for the cosmetic treatment of hair, characterized in that at least one composition as defined in claim 12 is applied to the hair.

18. Method for the cosmetic treatment of the skin, characterized in that a composition as defined in claim 13 is applied to the skin.

19. Dermatological composition in the form of an aqueous dispersion, characterized in that the aqueous dispersion is as defined in claim 9 and in that it contains, in an effective amount, at least one substance which is active at the dermatological level.

* * * * *